US006320124B1

United States Patent
Cheng

(10) Patent No.: US 6,320,124 B1
(45) Date of Patent: Nov. 20, 2001

(54) ELECTROPHYSIOLOGICAL FARADAY BOX

(75) Inventor: Henrich Cheng, Taipei (TW)

(73) Assignee: Veterans General Hospital - Taipei, Taipei (TW)

( * ) Notice: Subject to any disclaimer, the term of this patent is extended or adjusted under 35 U.S.C. 154(b) by 0 days.

(21) Appl. No.: 09/692,426

(22) Filed: Oct. 19, 2000

(30) Foreign Application Priority Data

Oct. 26, 1999 (TW) .............................................. 088218184

(51) Int. Cl.⁷ ..................................................... H05K 9/00
(52) U.S. Cl. ................................ 174/35 MS; 174/35 R; 361/816; 312/222.2
(58) Field of Search ......................... 174/48, 50, 35 MS, 174/35 R; 220/4.02; 361/816, 818, 753, 799; 312/222.2, 223.2

(56) References Cited

U.S. PATENT DOCUMENTS

| | | | |
|---|---|---|---|
| 4,760,496 | * | 7/1988 | Koch ................................ 174/35 R X |
| 5,294,748 | * | 3/1994 | Schwenk et al. .................. 361/816 X |
| 5,748,455 | * | 5/1998 | Phillips et al. ........................ 361/818 |
| 6,134,119 | * | 10/2000 | Gunther et al. ............... 174/35 MS X |
| 6,181,549 | * | 1/2001 | Mills et al. ......................... 312/223.2 |
| 6,188,015 | * | 2/2001 | Curran, Sr. et al. ............. 174/35 MS |
| 6,188,016 | * | 2/2001 | Enstrom et al. .................... 174/35 R |

FOREIGN PATENT DOCUMENTS

0120099 * 5/1989 (JP) ................................. 174/35 MS

* cited by examiner

Primary Examiner—Dean A. Reichard
Assistant Examiner—Dhiru R Palet
(74) Attorney, Agent, or Firm—Bacon & Thomas, PLLC

(57) ABSTRACT

An electrophysiological faraday box includes a main body, a work board, and a foldable door. The main body is able to provide an electromagnetically isolated space at the time when it is grounded by a bonding wire. The work board is mounted in the space of the main body and is an insulator. The foldable door is fastened to one side of the main body such that the foldable door can be opened partially or completely to enable a person to gain access to the work board. The foldable door is formed of a plurality of door units which are formed of metal screens electrically interconnected by a bonding wire. The side walls, the top, and the bottom of the main body are formed of framed metal screens electrically interconnected by a bonding wire.

3 Claims, 1 Drawing Sheet

ELECTROPHYSIOLOGICAL FARADAY BOX

FIELD OF THE INVENTION

The present invention relates generally to an electrophysiological faraday box for use in an animal electrophysiological experiment, and more particularly to an electrophysiological faraday box having an electromagnetic isolation main body, an electromagnetic isolation folding door, and an electrically insulated work table.

BACKGROUND OF THE INVENTION

In light of an animal subject being susceptible to interference by the electromagnetic wave, the experimental result of an animal electrophysiological experiment is often compromised. It is therefore imperative that such experiment must be carried out in an environment which is electromagnetic isolation to ensure that the animal subject is immune from the electromagnetic interference.

SUMMARY OF THE INVENTION

It is therefore the primary objective of the present invention to provide an electrophysiological faraday box which provides a space electromagnetically shielded.

It is another objective of the present invention to provide an electrophysiological faraday box which has an adjustable work space.

In keeping with the principle of the present invention, the foregoing objectives of the present invention are attained by the electrophysiological faraday box comprising:

an upright electromagnetic isolation main body which is provided with a bonding wire adapted to be grounded;

an electrically non-conductive work board mounted horizontally in said main body; and a foldable door fastened to one side of said main body such that said foldable door can be opened or closed partially or completely;

wherein said main body is provided in a top, a bottom, a left side, a right side, and a rear side with a metal frame and a metal screen held in said metal frame, wherein said metal screens of said main body are electrically interconnected by a bonding wire;

wherein said foldable door is formed of a plurality of door units, with each being formed of a metal frame and a metal screen held in said frame, wherein said metal screens of said door units of said foldable door are electrically interconnected by a bonding wire.

Preferably, said work board is mounted on the bottom of said main body.

Preferably, the electrophysiological faraday box of the present invention further comprises a base which is located under said main body for keeping articles.

The foregoing objectives, features, and functions of the present invention will be more readily understood upon a thoughtful deliberation of the following detailed description of a preferred embodiment of the present invention with reference to the accompanying drawing.

DETAILED DESCRIPTION OF A PREFERRED EMBODIMENT

Figure 1:
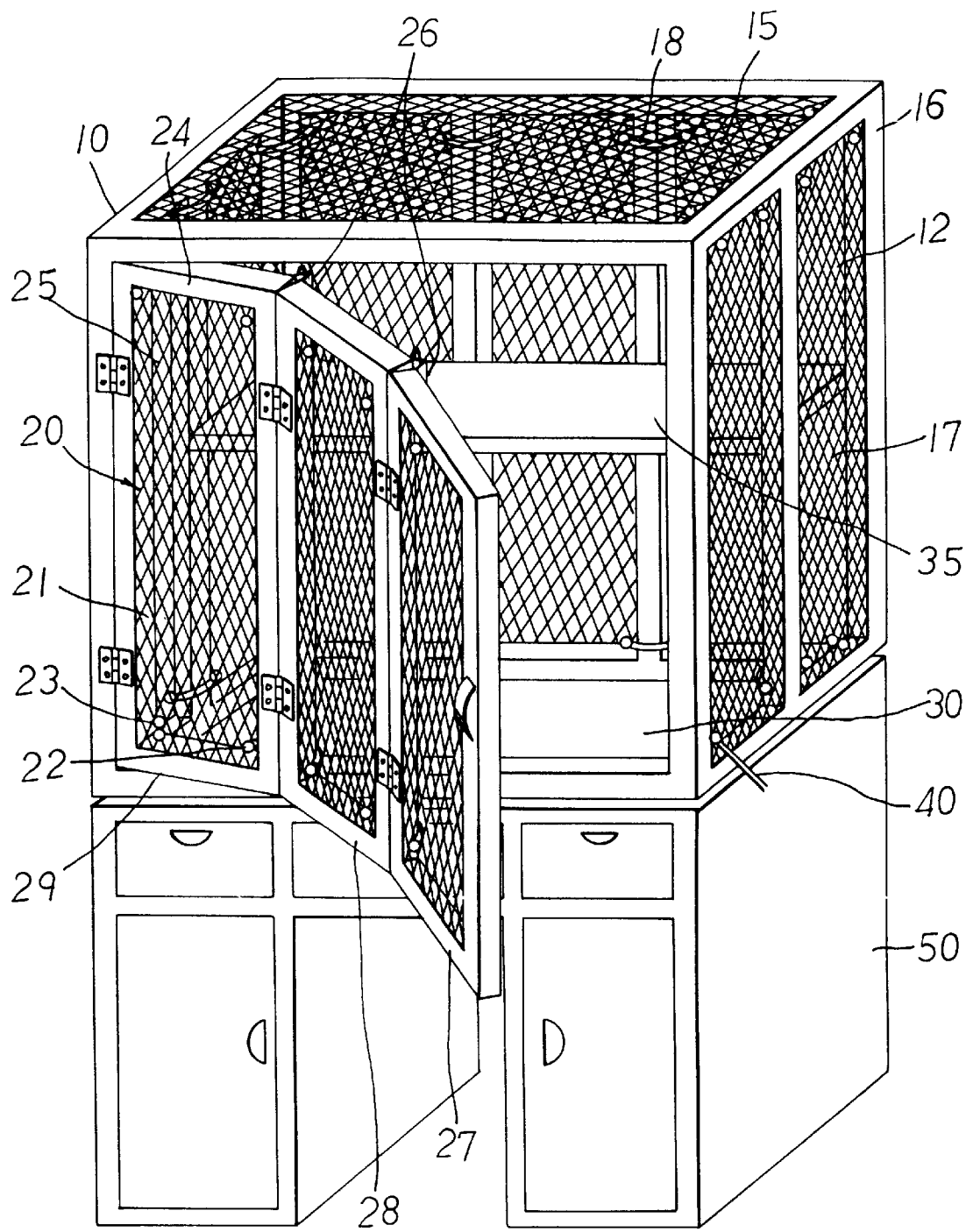
FIG. 1 shows a perspective view of an electrophysiological faraday box of the preferred embodiment of the present invention.

As shown in FIG. 1, the electrophysiological faraday box constructed according to one of the preferred embodiments of the present invention comprises an upright electromagnetic isolation main body 10, a foldable door 20, an electrically non-conductive horizontal work board 30, and a bonding wire 40 adapted to be connected with the ground.

With the exception of the foldable door 20, the top 15, the bottom (not shown in the drawing), and three side walls 12 of the main body 10 are made of a frame of aluminum alloy and a copper screen 17 which is held in the frame and is electroplated with chromium. The screens 17 of the side walls 12, the top 15, and the bottom are electrically interconnected with a bonding wire 18 fastened therewith by soldering. The screen 17 of one side wall is electrically connected with the bonding wire 40 which is connected with the ground.

The foldable door 20 is fastened to the fourth side of the main body 10 and is formed of three door units 21 which are hinged together. Each of the door units 21 is formed of a frame 24 of aluminum alloy and a copper screen 25 held in the frame 24 and electroplated with chromium. The screens 25 of the three screen units 21 are electrically interconnected by a bonding wire 22. The third door unit 29 of the foldable door 20 is hinged with the main body 10. A bonding wire 23 is provided to electrically connect the main body 10 and the foldable door 20. The second and third door units 28 and 29 are provided with a latch 26 for locking with the main body 10, so that the foldable door 20 can be opened or closed completely or only with the first door unit 27 being used.

The work board 30 is horizontally mounted on the bottom of and inside the main body 10. Further, an additional electrically non-conductive board 35 is horizontally mounted inside the main body 10 and above the work board 30 at a predetermined distance.

The present invention further comprises a base 50 which is located under the bottom of the main body 10 and is provided with a plurality of drawers and the like for keeping articles.

The experiment of the animal subject is done on the work board 30 without the interference of the electromagnetic wave. Depending on the requirements of the experiment, the foldable door 20 can be partially or fully opened, thanks to the first door unit 27, the second door unit 28, and the third door unit 29.

What is claimed is:

1. An electrophysiological faraday box comprising:

an upright electromagnetic isolation main body which is provided with a bonding wire adapted to be grounded;

an electrically non-conductive work board mounted horizontally in said main body; and a foldable door fastened to one side of said main body such that said foldable door can be opened or closed partially or completely;

wherein said main body is provided in a top, a bottom, a left side, a right side, and a rear side with a metal frame and a metal screen held in said metal frame, wherein said metal screens of said main body are electrically interconnected by a bonding wire;

wherein said foldable door is formed of a plurality of door units, with each being formed of a metal frame and a metal screen held in said frame, wherein said metal screens of said door units of said foldable door are electrically interconnected by a bonding wire.

2. The electrophysiological faraday box as defined in claim 1, wherein said work board is mounted on the bottom of said main body.

3. The electrophysiological faraday box as defined in claim 1 further comprising a base which is located under said main body for keeping articles.

* * * * *